US009302029B2

(12) United States Patent
Ganatra et al.

(10) Patent No.: US 9,302,029 B2
(45) Date of Patent: Apr. 5, 2016

(54) PULTRUSION OF POLY-4-HYDROXYBUTYRATE AND COPOLYMERS THEREOF

(71) Applicant: Tepha, Inc., Lexington, MA (US)

(72) Inventors: Amit Ganatra, Attleboro, MA (US); Bhavin Shah, Lowell, MA (US); Said Rizk, Windham, NH (US); David P. Martin, Arlington, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

(21) Appl. No.: 14/528,605

(22) Filed: Oct. 30, 2014

(65) Prior Publication Data

US 2015/0118152 A1    Apr. 30, 2015

Related U.S. Application Data

(60) Provisional application No. 61/898,144, filed on Oct. 31, 2013.

(51) Int. Cl.
| A61L 27/18 | (2006.01) |
| A61L 27/26 | (2006.01) |
| A61L 31/06 | (2006.01) |
| A61L 31/04 | (2006.01) |
| C08G 63/06 | (2006.01) |
| C08L 67/04 | (2006.01) |
| B29C 70/52 | (2006.01) |

(52) U.S. Cl.
CPC ............... *A61L 27/18* (2013.01); *A61L 27/26* (2013.01); *A61L 31/041* (2013.01); *A61L 31/06* (2013.01); *B29C 70/52* (2013.01); *C08G 63/06* (2013.01); *C08L 67/04* (2013.01)

(58) Field of Classification Search
CPC ....... A61L 27/18; A61L 27/26; A61L 31/041; A61L 31/06; B29C 70/52; C08G 63/06; C08L 67/04
See application file for complete search history.

(56) References Cited

U.S. PATENT DOCUMENTS

| 5,811,272 | A | 9/1998 | Snell |
| 6,245,537 | B1 | 6/2001 | Williams |
| 6,316,262 | B1 | 11/2001 | Huisman |
| 6,323,010 | B1 | 11/2001 | Skraly |
| 6,514,515 | B1 | 2/2003 | Williams |
| 6,548,569 | B1 | 4/2003 | Williams |
| 6,555,123 | B2 | 4/2003 | Williams |
| 6,585,994 | B2 | 7/2003 | Williams |
| 6,610,764 | B1 | 8/2003 | Martin |
| 6,623,749 | B2 | 9/2003 | Williams |
| 6,828,357 | B1 | 12/2004 | Martin |
| 6,838,493 | B2 | 1/2005 | Williams |
| 6,867,247 | B2 | 3/2005 | Williams |
| 6,867,248 | B1 | 3/2005 | Martin |
| 6,878,758 | B2 | 4/2005 | Martin |
| 7,025,980 | B1 | 4/2006 | Williams |
| 7,179,883 | B2 | 2/2007 | Williams |
| 7,244,442 | B2 | 7/2007 | Williams |
| 7,268,205 | B2 | 9/2007 | Williams |
| 7,553,923 | B2 | 6/2009 | Williams |
| 7,618,448 | B2 | 11/2009 | Schmitz |
| 7,641,825 | B2 | 1/2010 | Rizk |
| 8,016,883 | B2 | 9/2011 | Coleman |
| 8,034,270 | B2 | 10/2011 | Martin |
| 8,039,237 | B2 | 10/2011 | Martin |
| 8,231,889 | B2 | 7/2012 | Williams |
| 8,287,909 | B2 | 10/2012 | Martin |
| 2004/0234576 | A1* | 11/2004 | Martin ................ A61L 27/18 424/426 |
| 2005/0025809 | A1 | 2/2005 | Hasirci |
| 2005/0107578 | A1* | 5/2005 | Williams ............ C08K 5/0033 528/361 |
| 2007/0182041 | A1* | 8/2007 | Rizk et al. ........................ 264/6 |
| 2013/0085185 | A1 | 4/2013 | Guo |
| 2013/0150943 | A1* | 6/2013 | Zheng ................. A61L 27/58 623/1.2 |
| 2013/0218253 | A1 | 8/2013 | Kaufmann |
| 2013/0309166 | A1* | 11/2013 | Rizk et al. .................... 424/1.11 |

FOREIGN PATENT DOCUMENTS

| EP | 0802804 | 4/2002 |
| WO | 9932536 | 7/1999 |
| WO | 0056376 | 9/2000 |
| WO | 2005020825 | 3/2005 |
| WO | 2008070428 | 6/2008 |
| WO | 2011119742 | 9/2011 |
| WO | 2011159784 | 12/2011 |
| WO | 2012064526 | 5/2012 |
| WO | 2013098481 | 7/2013 |

OTHER PUBLICATIONS

Thangadurai, D., et al.; Biotechnology and Bioinformatics: Advances and Applications for Bioenergy, Bioremediation, and Biopharmaceutical Research, 2015, p. 286.*

(Continued)

*Primary Examiner* — Robert Jones, Jr.
(74) *Attorney, Agent, or Firm* — Pabst Patent Group LLP

(57) ABSTRACT

Compositions of P4HB (poly-4-hydroxybutyrate) and copolymers thereof, have been developed for pultrusion, as well as processes to produce profiles from these compositions by pultrusion. These pultrusion processes provide profiles without causing structural damage to the surface of the profile. The profiles may be used in medical applications. These compositions include P4HB, and copolymers thereof, having intrinsic viscosities less than 3.2 dl/g but greater than 0.8 dl/g. The profile may be formed using conditions such as: pull rate of 0.1 to 100 mm/min, die temperature of up to 95° C., rod stock temperature up to 95° C., draw ratio of up to 100×, pulling force of greater than 10 MPa, and clamping pressure at least 10% higher than the pulling force. Preferably, the profile is formed by pulling the rod stock through a series of dies placed at intervals with the hole sizes decreasing in diameter by 0.1 to 10 mm.

35 Claims, 2 Drawing Sheets

(56) References Cited

OTHER PUBLICATIONS

Bhowmick, A.K.; Current Topics in Elastomer Research, 2008, p. 233.*

Williams, S.F., et al.; Biomedizinische Technik/Biomedical Engineering, 2013, p. 1-14.*

Martin, D.P., et al.; Biochemical Engineering Journal, 2013, p. 97-105.*

Hori, et al., "Chemical synthesis of high molecular weight poly(3-hydroxybutyrate-co-4-hydroxybutyrate)", Polymer, 36:4703-5 (1995).

Houk, et al., "Why delta-valerolactone polymerizes and gamma-butyrolactone does not", J. Org. Chem., 73 (7), 2674-8 (2008).

Martin, et al., "Medical applications of poly-4-hydroxybutyrate: a strong flexible absorbable biomaterial", Biochem. Eng. J., 16:97-105 (2003).

Moore, et al., "Chemosynthesis of bioresorbable poly(gamma-butyrolactone) by ring-opening polymerisation: a review", Biomaterials, 26:3771-82 (2005).

Steinbüchel, et al., "Diversity of bacterial polyhydroxyalkanoic acids", FEMS Microbial. Lett.,128:219-28 (1995).

Williams, et al., "Applications of PHA\s in medicine and pharmacy", Polyesters, III, 4:91-127 (2002).

Williams, et al., "Poly-4-hydroxybutyrate (P4HB): a new generation of resorbable medical devices for tissue repair and regeneration", Biomed. Tech. (Berl), 58(5):439-52 (2013).

* cited by examiner

PULTRUSION OF POLY-4-HYDROXYBUTYRATE AND COPOLYMERS THEREOF

CROSS-REFERENCE TO RELATED APPLICATIONS

This application claims the benefit of priority to U.S. Ser. No. 61/898,144, filed on Oct. 31, 2013, the disclosure of which is incorporated herein by reference.

FIELD OF THE INVENTION

The present invention generally relates to pultrusion of poly-4-hydroxybutyrate and copolymers thereof, the compositions used in pultrusion, the processes used to produce products made by pultrusion, and methods to make medical implants from pultrusion products.

BACKGROUND OF THE INVENTION

Poly-4-hydroxybutyrate (P4HB, TephaFLEX® biomaterial) is a strong, pliable thermoplastic polyester that, despite its biosynthetic route, has a relatively simple structure. Upon implantation, P4HB hydrolyzes to its monomer, and the monomer is metabolized via the Krebs cycle to carbon dioxide and water. The polymer belongs to a larger class of materials called polyhydroxyalkanoates (PHAs) that are produced by numerous microorganisms (Steinbüchel, et al., *FEMS Microbial. Lett.* 128:219-228 (1995)). They are of commercial interest because of their thermoplastic properties, biodegradability and relative ease of production.

The PHA polymers have a diverse range of mechanical properties. For example, P4HB has entirely different physical and chemical properties from poly-3-hydroxybutyrate (P3HB, also commonly referred to as PHB) even though it belongs to the same polymer family. For example, P4HB has a melt temperature of 61° C. compared to a melt temperature of 180° C. for P3HB, and the elongation to break of P4HB is about 1,000% compared to just a few percent for P3HB. P4HB and P3HB also do not share the same molecular structure, and therefore have different crystallization rates, and whereas P4HB is a strong pliable and tough thermoplastic P3HB is a relatively brittle material. In fact, in terms of mechanical properties, P4HB has properties more similar to low density polypropylene than to the properties of P3HB.

Medical devices and applications of P4HB are disclosed by WO 00/56376 to Williams et al. Several patents including U.S. Pat. Nos. 6,514,515, 6,555,123, 6,585,994, 7,025,980, and WO 2005/020825 describe the use of PHAs in tissue repair and engineering.

In the practice of surgery there currently exists a need for resorbable structures with high tensile strength and high modulus. These structures must have prolonged strength retention, and be able to breakdown in vivo without releasing inflammatory products. U.S. Pat. Nos. 8,034,270, 8,016,883, 8,287,909, WO 2011/119742 and WO 2011/159784 disclose fibers, non-wovens, and textiles made by melt extrusion of P4HB. WO 2008/070428 discloses films made by solvent and melt extrusion of P4HB.

In contrast to melt extrusion processing (where polymer powder or pellets are melt extruded and oriented by stretching of the extrudate to form crystalline structures), pultrusion is a process whereby un-oriented polymeric rods are pulled through a series of profile dies to provide a reduced profile with high modulus and tensile strength. Thus, although P4HB has been extruded to produce, for example, films and fibers, as well as injection molding of P4HB, there is no disclosure of P4HB products made by pultrusion.

It is therefore an object of the present invention to provide compositions including P4HB and copolymers thereof, which can be processed by pultrusion to impart higher strength and stiffness without conventional stretching and without causing damage to the surface of the profile.

It is also an object of the invention to provide continuous processes for pultrusion of compositions including poly-4-hydroxybutyrate and copolymers thereof, which can be incorporated into, processed or formed into medical products with excellent physical and mechanical properties for medical applications.

It is another object of the present invention to provide a method of processing compositions of P4HB homopolymers, or copolymers thereof by pultrusion.

It is still another object of the present invention to provide profiles made from compositions of P4HB and copolymers thereof by pultrusion.

It is still further an object of the present invention to provide profiles of compositions of P4HB and copolymers thereof with enhanced mechanical properties and controlled degradation rates that can be used in medical applications.

SUMMARY OF THE INVENTION

Compositions of P4HB (poly-4-hydroxybutyrate), and copolymers thereof, have been developed for pultrusion, as well as processes to produce profiles from these compositions by pultrusion. Pultrusion processes provide profiles without causing structural damage to the surface of the profile. The profiles may be used in medical applications, such as implants, either directly or after further processing by techniques such as precision machining or thermoforming.

The compositions used for pultrusion include P4HB homopolymer, and copolymers thereof, with intrinsic viscosities less than 3.2 dl/g but greater than 0.8 dl/g. The P4HB polymers and copolymers may also be used as blends with other polymers and additives. The compositions of P4HB homopolymer and copolymers are formed into profiles, using pultrusion. In one embodiment, the compositions of P4HB homopolymer and copolymers are formed into rod stock, which is then formed into a profile. The rod stock has one or more of the following properties: tensile strength of 1-500 MPa, tensile modulus of 35-250 MPa, and elongation to break of less than 1,100%.

In embodiments where the starting polymer is P4HB homopolymer, the rod stock preferably has one or more of the following properties: tensile strength greater than 10 MPa, Young's modulus greater than 35 MPa, and elongation to break of less than 1,100%. In embodiments where the starting polymer is a P4HB copolymer, the rod stock preferably has one or more of the following properties: tensile strength greater than 1 MPa, Young's modulus greater than 35 MPa, and elongation to break of less than 500%.

The manufacture of profiles of P4HB, and copolymers and blends thereof, may be a two-step process where the rod stock is made first, and then the profile is made by pultrusion in a second discrete step. In this embodiment, compositions of P4HB, or copolymer/blend thereof, are preferably first extruded into pellets. Alternatively the profiles of P4HB polymers and copolymers thereof may be made using a multistage continuous process. In this embodiment, the extruded rod stock is cooled using a water bath prior to pultrusion. In one embodiment, the profile is formed using conditions selected from one or more of the following: pull rate of 0.1 to 100 mm/min, die temperature of up to 95° C., rod stock temperature up to 95° C., draw ratio of up to 100×, pulling force of greater than 5 MPa, and clamping pressure at least 10% higher than the pulling force. In a preferred embodiment, the profile is formed by pulling the rod stock through a series of dies placed at intervals with the hole sizes decreasing in diameter by 0.1 to 10 mm.

DETAILED DESCRIPTION OF THE INVENTION

Figure 1:
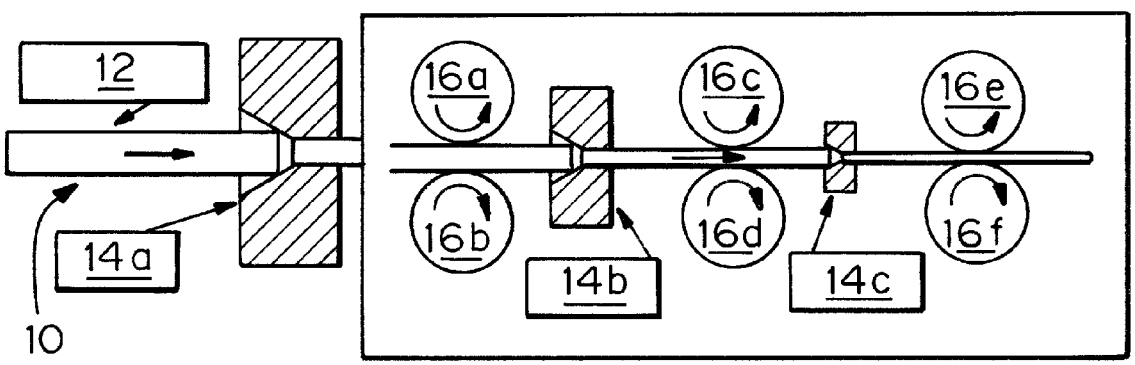
FIG. 1 is a schematic of a pultrusion process showing the rod stock being pulled by three pull rollers through three profile dies to form a profile.

It has been discovered that it is possible to use pultrusion to substantially increase the orientation of P4HB, resulting in increased modulus and tensile strength of the polymer, and a decrease in elongation to break of the processed polymer and devices made with the processed polymer, compared to the same polymer prior to orientation. Pultrusion is quite different from melt extrusion and orientation of P4HB fibers. Extrusion heats the polymer well above its melting temperature and pushes it through a die, maintained at a very high temperature (e.g. 180-250° C.), with pressure from a screw. In pultrusion, the polymer is not melted but is in the form of a rod much thicker than the fibers made by extrusion, and is pulled through a die. Typically the rod diameter will be greater than 0.78 mm². It has been discovered that precision machining of parts made by pultrusion, and thermal forming of parts made by pultrusion, can be used to make surgical implants.

I. Definitions

"Bioactive agent" is used herein to refer to therapeutic, prophylactic, and/or diagnostic agents. It includes without limitation physiologically or pharmacologically active substances that act locally or systemically in the body. A biologically active agent is a substance used for, for example, the treatment, prevention, diagnosis, cure, or mitigation of disease or disorder, a substance that affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, antibodies, sugars, polysaccharides, nucleotides, oligonucleotides, hyaluronic acid and derivatives thereof, aptamers, siRNA, nucleic acids, and combinations thereof.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer comprised of two or more different monomers.

"Copolymers of poly-4-hydroxybutyrate" as generally used herein means any polymer containing 4-hydroxybutyrate with one or more different hydroxy acid units.

"Draw ratio" as used herein means the ratio of the initial cross-sectional area of the rod stock to that of the final cross-sectional area of the profile. For example, in the case of a circular rod stock and profile, the draw ratio is 25× if the initial radius of the rod stock is 5 mm and the final radius of the profile is 1 mm.

"Implant" as generally used herein include medical devices that are used in vivo as well as those that contact the surface of the body or are inserted into any orifice of the body.

"Molecular weight" as used herein, unless otherwise specified, refers to the weight average molecular weight (Mw), not the number average molecular weight (Mn), and is measured by GPC relative to polystyrene.

"Rod stock" as used herein refers to the material before it is pulled through the die during pultrusion.

"Poly-4-hydroxybutyrate" as generally used herein means a homopolymer containing 4-hydroxybutyrate units. It may be referred to herein as P4HB or TephaFLEX® biomaterial (manufactured by Tepha, Inc., Lexington, Mass.).

"Profile" as used herein means a shape that has been produced by pultrusion.

"Pultrusion" as used herein means a process by which a composition including P4HB or copolymer thereof is pulled continuously through a die to yield a profile.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

As used herein, fibers have smaller diameters than rods. Rosato's Plastic Encyclopedia says fibers have a maximum cross sectional area of 0.05 mm². As used herein, fibers have cross sectional areas of up to 0.78 mm².

As used herein, films are thinner than sheets. Rosato's Plastic Encyclopedia defines a film as having a thickness of less than 10 mm. Sheets have a thickness of 10 mm or greater.

II. Compositions

Methods have been developed to process compositions of P4HB and copolymers and blends thereof for pultrusion. P4HB rod stock used in the pultrusion processes has also been developed. Processing these polymeric materials by pultrusion results in profiles which may be used as biocompatible implants, or may be converted to biocompatible implants through further processing.

(A) P4HB Polymers and Co-Polymers for Pultrusion

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, TephaFLEX® biomaterial) is a strong, pliable thermoplastic polyester that, despite its biosynthetic route, has a relatively simple structure as shown below.

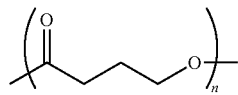

Upon implantation, P4HB hydrolyzes to its monomer, and the monomer is metabolized via the Krebs cycle to carbon dioxide and water.

The polymer belongs to a larger class of materials called polyhydroxyalkanoates (PHAs) that are produced by numerous microorganisms (Steinbüchel, et al., *FEMS Microbial. Lett.* 128:219-228 (1995)). In nature these polyesters are produced as storage granules inside cells, and serve to regulate energy metabolism. They are also of commercial interest because of their thermoplastic properties, biodegradability and relative ease of production.

The PHA polymers have a diverse range of mechanical properties. For example, P4HB has entirely different physical and chemical properties from poly-3-hydroxybutyrate (P3HB, also commonly referred to as PHB) even though it belongs to the same polymer family. For example, P4HB has a melt temperature of 61° C. compared to a melt temperature of 180° C. for P3HB, and the elongation to break of P4HB is about 1,000% compared to just a few percent for P3HB. P4HB and P3HB also do not share the same molecular structure, and therefore have different crystallization rates, and whereas P4HB is a strong pliable and tough thermoplastic P3HB is a relatively brittle material. In fact, in terms of mechanical properties, P4HB has properties more similar to low density polypropylene than to the properties of P3HB.

Numerous patent applications disclose the chemical synthesis of P4HB by ring-opening of gamma-butyrolactone, but provide no examples of the synthesis of P4HB polymer, except production of very low molecular weight oligomers which lack thermoplastic properties. It has been calculated to be thermodynamically impossible to chemically synthesize a high molecular weight homopolymer of P4HB with thermoplastic properties under normal conditions (see Hori, Y., et al., *Polymer* 36:4703-4705 (1995); Houk, K. N., et al., *J. Org. Chem.*, 2008, 73 (7), 2674-2678; and Moore, T., et al., *Biomaterials* 26:3771-3782 (2005)). Thus, the only source of P4HB is currently by fermentation of microorganisms.

U.S. Pat. Nos. 6,245,537, 6,623,749, 7,244,442, and 8,231,889 describe methods of making PHAs with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices.

Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al. and U.S. Patent Application No. 20130085185 to Kai et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, et al., *Polyesters, III*, 4:91-127 (2002), Martin, et al., *Biochem. Eng. J.* 16:97-105 (2003), and Williams, et al., *Biomed. Tech.* (Berl) 2013, ISSN (Online) 1862-278X, ISSN (Print) 0013-5585, DOI: 10.1515/bmt-2013-0009.

P4HB homopolymer can be obtained from Tepha, Inc. of Lexington, Mass., USA. Copolymers of P4HB include 4-hydroxybutyrate with one or more hydroxyacid monomers. Examples of P4HB copolymers include copolymers of 4-hydroxybutyrate with 3-hydroxybutyrate, and with 2-hydroxy acids such as glycolic acid and lactic acid monomers.

In a particularly preferred embodiment, the P4HB and copolymers thereof have intrinsic viscosities of between 0.8 and 3.2 dl/g. The intrinsic viscosity of the P4HB and copolymers thereof may be determined using an Agilent 1100 Series HPLC equipped with an Agilent triple detector system (Agilent 390-LC Multi Detector Suite). The triple detector is equipped with a laser light scattering (LS) detector, a refractive index (RI) detector and a viscosity (Vis) detector. Samples of polymer may be prepared at 1 mg/ml in chloroform, and 100 µl of these solutions injected onto a Polymer Labs, PLgel column (5 micron, mixed C, 300×7.5 mm), and eluted at 1 ml/min. Intrinsic viscosity values may be determined using the Cirrus™ GPC/Multi Detector Software.

(i) Additional Polymers

The compositions for pultrusion may include the P4HB homopolymer or copolymer blended with other absorbable polymers. Other absorbable polymers include, but are not limited to, poly(lactides); poly(glycolides); poly(lactide-co-glycolides); poly(lactic acid); poly(glycolic acid); poly(lactic acid-co-glycolic acids); polycaprolactones; poly(orthoesters); polyanhydrides; poly(phosphazenes); polyhydroxyalkanoates (including PHB, PHBV, and P4HB copolymers); synthetically or biologically prepared polyesters (including polyesters with one or more of the following monomeric units: glycolic, lactic; trimethylene carbonate, p-dioxanone, or ε-caprolactone); poly(lactide-co-caprolactones); polycarbonates; tyrosine polycarbonates; polyamides (including synthetic and natural polyamides, polypeptides, and poly (amino acids)); polyesteramides; poly(dioxanones); poly (alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; collagen; silk; biocompatible polysaccharides; biocompatible copolymers (including block copolymers or random copolymers); hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide, or polycaprolcatone or combinations thereof.

(ii) Reinforcing Elements

If desired, the compositions for pultrusion may also incorporate reinforcing elements to improve the properties of the profiles. Such reinforcing elements may be used to improve properties such as tensile strength and Young's modulus. In a preferred embodiment, the reinforcing elements are resorbable biocompatible fibers. In a particularly preferred embodiment, the reinforcing elements are fibers of polymers with monomers selected from glycolic acid, lactic acid, trimethylene carbonate, p-dioxanone, and ε-caprolactone.

(B) Rod Stock for Pultrusion

The P4HB homopolymer, copolymer or blend is formed into a rod stock for pultrusion. In a preferred embodiment, the P4HB, or copolymer/blend composition is first extruded into pellets or granules. These pellets can then be used to produce the rod stock. In a particularly preferred embodiment, the pellets or granules made of P4HB homopolymer, or copolymers/blends thereof, suitable for extrusion or molding into rod stock have intrinsic viscosities ranging from 0.8 to 3.2 dl/g, and more preferably from 1.0 to 2.5 dl/g. In particular the intrinsic viscosity of the polymer pellets or granules should not be less than 0.8 or greater than 3.2 dl/g.

The rod stock may have one or more of the following properties: tensile strength of 1-500 MPa, tensile modulus of 35-250 MPa, and elongation to break of less than 1,100%. In embodiments where the starting polymer is P4HB homopolymer, the rod stock preferably has one or more of the following properties: tensile strength greater than 10 MPa, Young's modulus greater than 35 MPa, and elongation to break of less than 1,100%. In embodiments where the starting polymer is a P4HB copolymer, the rod stock has one or more of the following properties: tensile strength greater 1 MPa, Young's modulus greater than 35 MPa, and elongation to break of less than 500%.

(i) Incorporation of Additives into Compositions for Pultrusion

Certain additives may be incorporated into the compositions for pultrusion prior to or during the formation of the rod stock. Preferably, these additives are incorporated during a compounding process to produce powder or pellets that can be processed into rod stock. In a preferred embodiment, the additives are biocompatible, and even more preferably the additives are both biocompatible and resorbable.

The additives may be nucleating agents and/or plasticizers. These additives are added in sufficient quantity to produce the desired result. In general, these additives may be added in amounts of up to 20% by weight. Nucleating agents may be incorporated to increase the rate of crystallization of the P4HB homopolymer, copolymer or blend. Such agents may be used to improve the mechanical properties of the rod stock. Preferred nucleating agents include, but are not limited to, salts of acceptable organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine Plasticizers that may be incorporated include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis (2-hydroxyethyl)dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tributyl phosphate, and mixtures thereof. Particularly preferred plasticizers are citrate esters.

Additional additives that can be included in the compositions include contrast agents, radiopaque markers and radioactive substances. Additives such as ceramics, preferably resorbable biocompatible ceramics can also be used with the P4HB polymer compositions and blend. Examples of resorbable bioceramics include tricalcium phosphate [α and β forms of TCP—with a nominal composition of $Ca_3(PO_4)_2$], calcium sulfate, calcium carbonate, and other calcium phosphate salt-based bioceramics. Bio-active glasses may also be used. Bioactive glasses are composed of $SiO_2$, $Na_2O$, $CaO$ and $P_2O_5$ in specific proportions. The choice of bioceramic and particle size of the bioceramic will depend in part on the desired rate of resorption for the implant. In a preferred embodiment, the bioceramic is β-TCP, α-TCP or a combination thereof with a nominal particle size of 20 microns. In further embodiments, the particles may have a size or distribution between 0.1 and 500 microns.

(ii). Compounding of P4HB Homopolymer, Copolymers and Blends Thereof with Bioactive Agents If desired, rod stock made from P4HB homopolymer, P4HB copolymers or P4HB blends may incorporate bioactive agents. These agents may be added during a formulation process, during a pelletization process, or may be added later to the rod stock or profile by coating or impregnating the rod stock or profile. If desired, the bioactive agents may be dissolved in a solvent or solvent system in order to disperse the bioactive agent in the P4HB polymer, copolymer, or blend thereof, or for use as a coating on the rod stock or profile, and the solvent may then be removed by evaporation. Preferred solvents include methylene chloride, chloroform, dichloroethane, tetrachloroethane, trichloroethane, dibromomethane, bromoform, tetrahydrofuran, acetone, dimethylformamide, and 1,4-dioxane.

C. Profiles of P4HB Polymers and Copolymers Produced by Pultrusion

Profiles produced by pultrusion of compositions of P4HB and copolymers thereof, can be used either directly or after further processing for medical applications. The profiles have one or more of the following properties: a tensile strength up to about 1 GPa, a maximum modulus of up to about 0.5 GPa, and a minimum elongation to break of about 50%.

The products of pultrusion can be used in many types of medical applications including orthopedic, craniomaxillofacial, dental, and cardiovascular, as well as in cardiology, plastic and reconstructive surgery, general surgery, ear, nose and throat surgery, and oral surgery.

The profiles can be further processed in medical applications, including implants, including for example, devices such as suture anchors, screws, pins, including locking pins, wires, bone plates, interference screws, tacks, nails, fasteners, rivets, staples, medullary cavity nails, clips, clamps, tubes, tissue engineering scaffolds, rotator cuff repair devices, meniscus repair devices, guided tissue repair/regeneration devices, articular cartilage repair devices, tendon repair devices, ligament repair devices, fixation devices for an implant, plastic surgery devices (including devices for fixation of facial and breast cosmetic and reconstructive devices), fixation devices for surgical meshes, facial reconstructive devices, spinal fusion devices, devices for treatment of osteoarthritis, imaging devices, and bone graft substitutes.

III. Methods of Making Rod Stock for Pultrusion

Rod stock for pultrusion may be made by any suitable method including melt extrusion, injection molding, thermoforming, or solvent casting/spinning. A particularly preferred method of forming the rod stock is by extrusion. The rod stock may be formed by melt processing directly from a powder or granular form of the composition, however, in a preferred embodiment, the P4HB homopolymer, or copolymer/blend thereof, is first extruded into pellets. Pellets of P4HB homopolymer, or copolymer/blends thereof, may be compounded by metering in the desired ratio of polymers (as well as any additives) into a single or twin-screw extruder, wherein they are mixed prior to being extruded into pellets. These pellets can then be used to produce the rod stock by further melt processing, preferably using melt extrusion.

Prior to extrusion of the rod stock, the compositions of P4HB, or copolymers/blends thereof, should be dried since it has been found that the polymers are sensitive to the presence of moisture at high temperatures, particularly if exposed to these conditions for prolonged periods. Prolonged exposure of the compositions to elevated temperatures in the presence of moisture results in a significant loss of plastic viscosity. The amount of drying necessary depends on the loss of intrinsic viscosity that can be tolerated for any particular application of the profile. In a preferred embodiment, the compositions are dried to moisture contents of less than 0.5% by weight as measured gravimetrically, and more preferably less than 0.05% by weight, prior to extrusion. The compositions may be dried in vacuo, for example, using a rotary vane vacuum pump system. In a preferred method, the polymer or blend is dried in a vacuum chamber under a vacuum of at least 10 mbar (7.5 mmHg), more preferably of at least 0.8 mbar (0.6 mmHg), to a moisture content of less than 0.03% by weight. Elevated temperatures below the melting point of the polymer may also be used in the drying process. Alternatively, the polymer may be dried by extraction into a solvent and re-precipitation, or with the use of desiccants.

The moisture content of samples of P4HB and copolymers/blends thereof may be determined using a VaporPro Moisture Analyzer from Arizona Instruments, or similar instrument, as follows. Samples should be transferred to test vials in a low humidity environment (<5% RH) to minimize pickup of ambient moisture. Samples (1 g) can then be heated to 120° C. under a purge of dry nitrogen. The moisture content of the purge gas is determined by the Vapor Pro and reported as a % of the sample weight.

The rod stock may be produced using an extruder set up with an appropriate die. For example, a single hole spinneret for producing rod stock of a specific diameter. The cross-section of the die may be tailored to the intended application, or designed for subsequent processing, for example, by precision machining. The cross-section may be any desired shape. In one embodiment, the rod stock is produced using an extruder barrel with a 1.5 in (38 mm) diameter fitted with an extrusion screw with a 30:1 L/D ratio, and 5 heating zones. For processing, the heating zones may be set at temperatures from 40° C. to 260° C., and pressures set at 400 psi (2.76 MPa) to 2000 psi (13.8 MPa). Pellets are gravity fed into a chilled feeder section, introduced into the extruder barrel, and the heated and softened resin fed into a heated metering pump (melt pump), and then into a heated block and a single hole spinneret assembly. The molten rod stock may be water quenched in chilled water before the rod stock is collected. The rod stock produced as described herein has one or more of the following properties: tensile strength of 1-500 MPa, tensile modulus of 35-250 MPa, and elongation to break of less than 1,100%.

IV. Methods of Pultrusion

The manufacture of profiles of P4HB, and copolymers and blends thereof, may be a two-step process wherein the rod stock is made first, and then the profile is made by pultrusion in a second discrete step. Or, alternatively these two processes can be combined into a multistage continuous process. In the latter case, the extruded rod stock is cooled preferably using a water bath prior to pultrusion.

In contrast to melt extrusion of P4HB and copolymers thereof wherein dies are typically heated to 180-250° C. (U.S. Pat. No. 7,641,825 to Rizk), in a preferred embodiment, the rod stock is pulled at ambient temperature through the die assembly with the die assembly also at ambient temperature. The rod stock may also be heated to no more than 45° C. and pulled through the die assembly, wherein the die assembly is at ambient temperature. In another embodiment, the rod stock and the die assembly are both heated. In this embodiment, it was determined that the rod stock may be heated to temperatures as high as 95° C., even though the melt temperature of P4HB is just 61° C., provided that the rod stock is under tension. During melt extrusion, the polymer is not being oriented, is not under tension, and is thermally stable to about 250° C. In pultrusion, the polymer is being oriented while under tension. If the polymer is heated above its melt temperature during pultrusion without being under tension it will lose orientation and melt. Extrusion is a push process for molten polymer whereas pultrusion is a pull process on a solid form. More preferably, the rod stock and sizing (profile) die assembly may be heated to 40-75° C.

Figure 2:
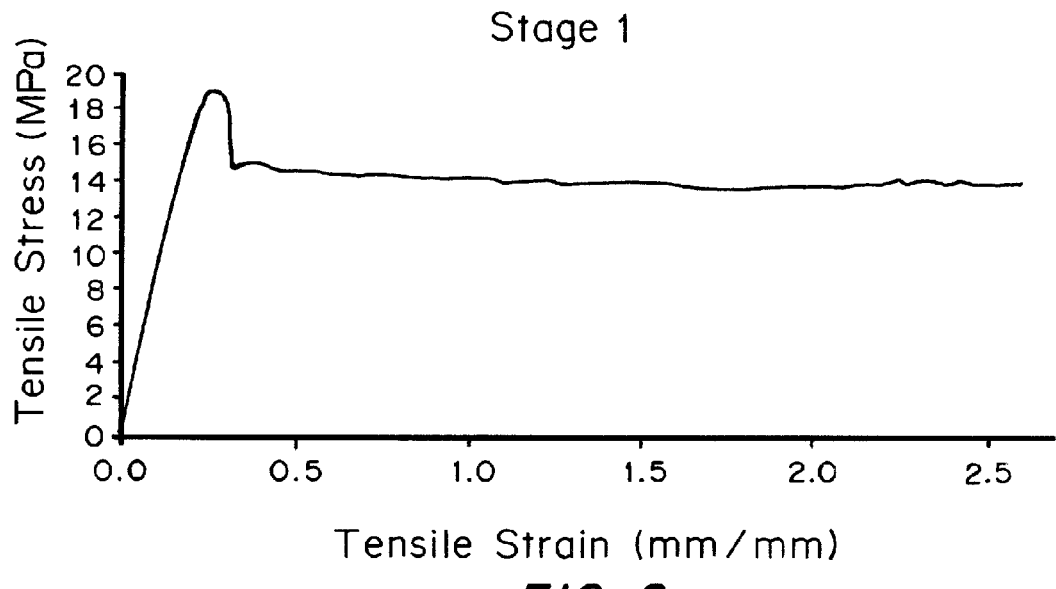
FIG. 2 is a stress-strain curve showing the yield of an un-oriented P4HB rod stock with an initial diameter of 4.8 mm.

In a typical procedure for pultrusion of P4HB, and copolymers and blends thereof, the pultrusion process uses controlled processing conditions of temperature, pulling force, profile clamp pressure, and pulling speed, wherein the rod stock is pulled through a die to form the profile. The basic equipment set up necessary for pultrusion of P4HB, and copolymers and blends thereof, shown in FIG. 2, includes a conveyer 10 for the rod stock 12, a die (14a, 14b, 14c), a puller (16a-16f), and a saw or other device to cut the profile to the desired length. FIG. 2 shows one suitable setup of dies and rollers for pultrusion of P4HB, and copolymers and blends thereof, wherein the rod stock 12 is pulled by three pull rollers 16a-16f through three profile dies 14a, 14b, 14c to form a profile. Additional components that can be incorporated into the equipment set up include an oven to preheat or control the temperature of the rod stock, a heater for the die, and equipment to cool the profile if the pultrusion process is run at elevated temperature. In an embodiment, the rod stock is pulled through the die to form the profile. In another embodiment, the puller is either a caterpillar counter-rotating type or a hand-over-hand pulling device.

A. Die Assembly Design

It has been discovered that the design of the die and the pulling speed are critical to the successful production of profiles with smooth (unbroken) surfaces. In a preferred embodiment, the rod stock is pulled through a series of dies, or a sizing die, to ensure that the surface of the polymer is not damaged. By carefully decreasing the diameter of successive dies it is possible to produce profiles of P4HB, copolymers, and blends thereof, without surface damage. It should be noted that the surface of the rod stock draws more than the center section of the rod stock elevating the risk of damage to the surface during passage through the die. In a preferred embodiment, two or more dies are used for pultrusion with each successive die having a slightly smaller diameter hole such that the rod stock is pulled through a series of dies with decreasing hole sizes.

In an embodiment, a series of dies with hole sizes decreasing in diameter by 0.1 to 10 mm are placed at intervals, and the rod stock is pulled through these dies to form the profile. In a preferred embodiment, the hole sizes of the series of dies decrease by 0.5 to 5 mm in diameter. The spacing between the dies may be adjusted to prevent damage to the surface of the profile. In a preferred embodiment, the dies are spaced at 0.5 to 500 cm, and more preferably at 2 to 100 cm.

B. Pulling Speed

Production of profiles of P4HB, and copolymers and blends thereof, without surface damage also requires careful control of the pulling speed in addition to appropriate selection of the die assembly. It has been discovered that the profile will undergo surface damage or rupture if the rod stock is pulled through the die assembly too fast. The optimum pulling speed will depend on the specific die setup (die assembly) used in the process, the diameter of the rod stock, and whether the die is heated. If the difference in the cross-section between the rod stock and the hole size of the die is relatively small, for example, if the difference in cross-sections between the die and the rod stock is less than 25%, or the difference in diameters between the die and the rod stock is no more than 1 mm, high pulling speeds of over, for example, 1 m/min are possible. However, slower pulling speeds will be necessary if the cross-section of the profile is substantially less than that of the rod stock, for example, if the difference in cross-sections must be larger than 25%, in order to avoid rupture or damage to the surface of the profile. In one embodiment, the pulling speed is between 1 mm/min and 1 m/min, more preferably between 1 mm/min and 100 mm/min, and even more preferably between 1 mm/min and 10 mm/min.

The properties of the profile of P4HB, and copolymers and blends thereof, will depend on the draw ratio defined as the ratio of the length of the drawn rod stock to that of the length of the undrawn profile. In an embodiment, the draw ratio may be as high as 50× without heating the rod stock or the die assembly, or by applying heat to the rod stock and die assembly. In another embodiment, the draw ratio may be as high as 100× provided both the rod stock and die assembly are heated during pultrusion.

The pulling force required to make the profiles is dependent upon the cross-section of the rod stock, the desired draw ratio, and the temperature. A higher pulling force is required as the cross-section of the rod stock and draw ratio are increased. For example, a rod stock with an 8 mm diameter requires a pulling force of around 10 MPa increasing to 500 MPa to achieve a draw ratio of 50× during stretching at ambient temperature. Further drawing of the rod stock beyond a draw ratio of 50× requires elevated temperatures and a draw force in excess of 500 MPa. Pulling forces as high as 5,000 MPa or more can be required for pultrusion of large cross-section rod stock particularly when high draw ratios are desired.

The clamping pressure required to make the profiles of P4HB, and copolymers and blends thereof, must be set higher than the pulling force used to make the profile. In an embodiment, the clamping pressure is at least 10% higher than the pulling force, and more preferably at least 20% higher than the pulling force. For example, pultrusion of the 8 mm diameter rod stock described above using a draw force in excess of 500 MPa would preferably require a clamping pressure greater than 600 MPa.

The mechanical properties of the profiles produced by pultrusion of compositions containing P4HB, and copolymers and blends thereof, are dependent upon the draw ratio. For example, at a draw ratio of 40×, the tensile strength and elongation to break of the profile are approximately 175 MPa and 550%, respectively. As the draw ratio is increased further and the elongation to break decreases to 50-100%, the tensile strength can increase to approximately 1 GPa, and the Young's modulus increases to 0.5 GPa. In comparison, an unoriented sample of P4HB typically has an elongation to break of approximately 1,000%, a tensile strength of 50 MPa, tensile modulus of 70 MPa, and a hardness of 53 measured on the Shore D scale.

The profiles produced by pultrusion may be annealed to increase their crystallinity content by exposure to temperatures preferably of 45-55° C. In an embodiment, the profiles are annealed by heating in a water bath. The ratio of crystallinity/amorphous content may also be manipulated by annealing the profiles in a post molding heat cycle.

V. Methods for Post-Pultrusion Processing of Profiles to Make Medical Devices Medical device implants made from pultrusion of P4HB, and copolymers and blends thereof, have substantially improved properties for many medical applications relative to the same compositions made from brittle degradable thermoplastics. In particular, these implants have improved toughness that prevents breakage of the implant either during implantation or prior to the conclusion of healing. Toughness is the ability of the material to absorb energy. The key to high toughness is that a material must have high strength and high ductility. The implants made from P4HB by pultrusion have both high strength and high ductility. In contrast, other compositions, such as PLA and PGA, are brittle and although they have high strength they have low ductility. A material with high strength and high ductility is tougher than a material with high strength and low ductility.

The use of implants with lower intrinsic viscosities is particularly advantageous because the resorption time in vivo of these implants is faster than for implants having higher intrinsic viscosities. By careful selection of the intrinsic viscosity of the starting polymer composition, and control of pultrusion processing parameters, it is possible to produce implants with a range of different intrinsic viscosities, and therefore tailor the resorption rates to different applications. In one embodiment, implants with an intrinsic viscosity of less than 3.2 dl/g, but greater than 0.8 dl/g, are preferred.

The profiles produced by pultrusion of P4HB, and copolymers and blends thereof, can be used directly in medical devices, for example, as rods and pins, or further processed to make medical devices. In an embodiment, the profiles may be machined to provide different shaped implants. In another embodiment, the profiles may be cut with a laser in order to provide the desired implant shape. In yet another embodiment, the profiles may be further processed into implants by thermal forming.

Medical device implants made by pultrusion of compositions of P4HB homopolymers, copolymers and blends thereof, may be used for soft and hard tissue repair, regeneration, and replacement using processing methods known in the art. Implants made from profiles of P4HB, and copolymers and blends thereof, may be used in the following medical devices, including but not limited to: suture anchors, screws, pins, including locking pins, wires, bone plates, interference screws, tacks, nails, fasteners, rivets, staples, medullary cavity nails, clips, clamps, tubes, tissue engineering scaffolds, rotator cuff repair devices, meniscus repair devices, guided tissue repair/regeneration devices, articular cartilage repair devices, tendon repair devices, ligament repair devices, fixation devices for an implant, plastic surgery devices (including devices for fixation of facial and breast cosmetic and reconstructive devices), fixation devices for surgical meshes, facial reconstructive devices, spinal fusion devices, devices for treatment of osteoarthritis, imaging devices, and bone graft substitutes.

The present invention will be further understood by the following non-limiting examples.

Example 1

Pelletization of P4HB Homopolymer and Drying

Materials and Methods

P4HB granules with an intrinsic viscosity of 2.18 dl/g, and a moisture content no greater than 0.03% by weight after vacuum drying, were pelletized using a co-rotating fully intermeshing twin screw extruder with a screw diameter of 27 mm, length to diameter ratio of 40/1, screws rotating at 125-135 rpm, and with the barrel temperature of the extruder increasing from 100° C. at the feed zone to 210° C. at the die. The feed throat of the extruder was water cooled to 30° C. The P4HB granules were added directly to a loss-in-weight feeder, and fed to the extruder at a feed rate of 3.0 kg/hr. The extrudate was quenched immediately in cold water at 10° C., and once sufficiently cooled was cut into pellets using a pelletizer.

Results

The method yielded P4HB pellets with an intrinsic viscosity of 2.01 dl/g. The loss of intrinsic viscosity on pelletization was 7.8%.

Example 2

Extrusion of P4HB Rod Stock

Rod stock made of P4HB was extruded using a single stream spinneret with a L/D of 16:1 and a hole diameter of 9.5 mm. P4HB pellets were dried to less than 0.03 wt % water using a rotary vane vacuum pump system, and transferred to an extruder feed hopper with nitrogen purge to keep the pellets dry. The pellets were gravity fed into a chilled feeder section and introduced into the extruder barrel, which was 1.50 in (38 mm) in diameter and fitted with an extrusion screw with a 30:1 L/D ratio. The extruder barrel contained 5 heating zones (or extrusion zones)—zones 1, 2, 3, 4 and 5, and was manufactured by American Kuhne. The heated and softened resin from the extruder was fed into a heated metering pump (melt pump) and from the melt pump the extruded resin was fed into the heated block and the single hole spinneret assembly. Heat zones 1-5 were set at 60, 185, 210, 240, and 235° C., respectively, and the block, pump and spin pack were set at 240, 245 and 255° C., respectively. The pump pressure was set at 1400 psi (9.65 MPa), and the polymer flow rate and melt density were 13.25 g/min and 1.08 g/cm$^3$, respectively. The molten rod stock was water quenched at 12° C., and cut into 1 m long sections that had a diameter of 7.5 mm.

Example 3

Pultrusion of P4HB Rod Stock

The P4HB rod stock produced in Example 2 can be used to manufacture a profile by pultrusion using a sizing die to draw down the 7.5 mm rod stock. In order to produce the profile without damaging the surface of the polymer, the die assembly can be designed to reduce the diameter of the rod stock in stages so that at each stage the diameter of the rod stock is reduced by 1 mm. The distance between the dies in the assembly is preferably about 50 cm. The rod stock may be drawn through the dies using a pulling force between 10 and 500 MPa at ambient temperature, and a clamping pressure at least 20% higher than the pulling force.

Example 4

Orientation of P4HB Rod Stock

Materials and Methods

A P4HB rod stock with an initial diameter of 4.8 mm, produced using a similar procedure to that described in Example 2, was pulled in two stages using an Instron fitted with a 100 KN load cell at a rate of 12.5 mm/min, and a gauge length of 40.13 mm. In the first stage, the rod stock was pulled at ambient temperature, and necking of the rod stock was observed after the initial stress rise. The necking was characterized by a localized extension at an axial position along the sample, and a corresponding decrease in cross-sectional area. Pulling was continued until the decrease in cross-sectional area was all along the draw axis.

Results

The diameter of the sample at two stresses was calculated from the stress-strain curve shown in FIG. 2, and is reported in Table 1. A transition from elastic yield to plastic region was noted when the pull stress decreased from 19.04 MPa to 14.4 MPa and the diameter decreased from 4.26 mm to 2.53 mm.

TABLE 1

Diameter vs Stress During Orientation of P4HB Rod Stock

| Diameter (mm) | 4.8 | 4.26 | 2.53 |
|---|---|---|---|
| Stress (MPa) | 0 | 19.04 | 14.14 |

Figure 3:
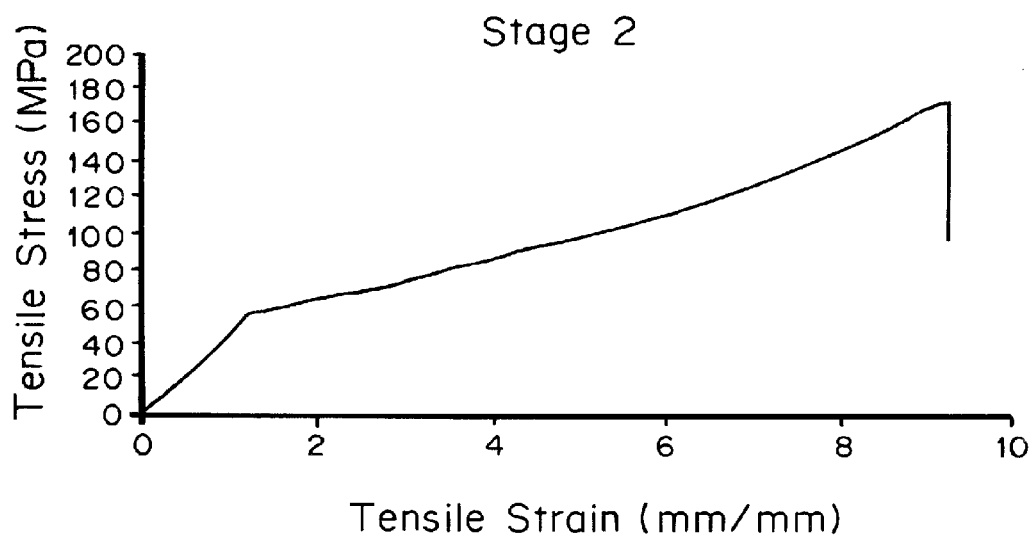
FIG. 3 is a stress-strain curve showing the yield of semi-oriented P4HB rod stock with an initial diameter of 2.67 mm.

After drawing in the first stage, the diameter of the P4HB sample increased to 2.67 mm when the drawing forces were removed. In the second stage, a section of the rod drawn in the first stage was drawn again using a gauge length of 30.48 mm and the same load cell. As in the first stage, the stress-strain curve was plotted (see FIG. 3), and the diameter of the sample was calculated (see Table 2). Notably, the diameter of the P4HB sample increased to 1.97 mm due to an increase in entropy when the drawing stresses were removed.

TABLE 2

Diameter vs Stress During Orientation of Semi-oriented P4HB Rod Stock

| Diameter (mm) | 2.67 | 1.46 | 0.97 | 0.83 |
|---|---|---|---|---|
| Stress (MPa) | 0 | 67.03 | 120.03 | 171.00 |

We claim:

1. A profile made by pultrusion of a composition comprising a polymer wherein the polymer consists of poly-4-hydroxybutyrate wherein the profile has a tensile strength between 175 MPa and 1 GPa, wherein a rod stock of the composition is pulled through one or more dies to form the profile.

2. The profile of claim 1 wherein the rod stock is pulled at a rate between 0.1 and 100 mm/min.

3. The profile of claim 1 wherein the temperature of the die or dies is 95° C. or less.

4. The profile of claim 1 wherein the rod stock is heated up to a temperature of 95° C.

5. The profile of claim 4 wherein the heated rod stock is above the melting point of the composition and under tension.

6. The profile of claim 1 wherein the temperature of the rod stock and one or more dies is from 40 to 75° C.

7. The profile of claim 1 wherein the draw ratio is up to 50× and the rod stock is not heated.

8. The profile of claim 1 wherein the draw ratio is up to 100× and the rod stock is heated and under tension.

9. The profile of claim 1 wherein the composition has an intrinsic viscosity of 0.8 to 3.2 dl/g.

10. The profile of claim 1 wherein the rod stock has an elongation to break of less than 1,100%, a tensile strength greater than 10 MPa, and a Young's modulus greater than 35 MPa.

11. The profile of claim 1 wherein the profile has an elongation to break from 50-100%.

12. The profile of claim 1 wherein the rod stock is pulled with a pulling force of at least 10 MPa.

13. The profile of claim 12 wherein the rod stock is clamped during pulling, and the clamping pressure is 10% higher than the pulling force.

14. The profile of claim 1 wherein there is more than one die, and the dies are placed at intervals of 0.5 to 500 cm.

15. The profile of claim 1 wherein there is a series of dies placed at intervals with hole sizes decreasing in diameter by 0.1 to 10 mm, and the rod stock is pulled through these dies to form the profile.

16. The profile of claim 1 wherein the cross-sectional area of the rod stock is greater than 0.78 mm².

17. The profile of claim 1 wherein the composition further comprises nucleant, plasticizer, reinforcing element, bioactive agent, ceramic, contrast agent, radiopaque marker and/or radioactive substance.

18. The profile of claim 1 wherein the surface of the profile is not damaged during pultrusion.

19. A medical device produced from the profile of claim 1.

20. The device of claim 19 wherein the device is produced by machining, thermally forming or laser cutting of the profile.

21. The device of claim 19 wherein the device is used for soft and hard tissue repair, regeneration, and replacement.

22. The device of claim 21 selected from the group consisting of suture anchors, screws, pins, including locking pins, wires, bone plates, interference screws, tacks, nails, fasteners, rivets, staples, medullary cavity nails, clips, clamps, tubes, tissue engineering scaffolds, rotator cuff repair devices, meniscus repair devices, guided tissue repair/regeneration devices, articular cartilage repair devices, tendon repair devices, ligament repair devices, fixation devices for an implant, plastic surgery devices, breast cosmetic and reconstructive devices), fixation devices for surgical meshes, facial reconstructive devices, spinal fusion devices, devices for treatment of osteoarthritis, imaging devices, and bone graft substitutes.

23. The device of claim 19 further comprising one or more of the following:
   bioactive agent, ceramic, contrast agent, radiopaque marker and radioactive substance.

24. A method of using the device of claim 19, wherein the device is implanted in the body or applied topically to the surface of the body.

25. A method of forming a profile of a composition comprising a polymer by pultrusion wherein the polymer consists of poly-4-hydroxybutyrate thereof, and wherein the profile has a tensile strength between 175 MPa and 1 GPa, comprising pulling a rod stock of the composition through one or more dies at a rate between 0.1 and 100 mm/min, to form the profile.

26. The method claim 25 wherein the temperature of the die or dies is 95° C. or less.

27. The method of claim 25 wherein the rod stock is heated up to a temperature of 95° C.

28. The method of claim 27 wherein the heated rod stock is above the melting point of the composition and under tension.

29. The method of claim 25 wherein the temperature of the rod stock and one or more dies is from 40 to 75° C.

30. The method of claim 25 wherein the draw ratio is up to 50× and the rod stock is not heated.

31. The method of claim 25 wherein the draw ratio is up to 100× and the rod stock is heated and under tension.

32. The method of claim 25 wherein the rod stock is pulled with a pulling force of at least 10 MPa.

33. The method of claim 32 wherein the rod stock is clamped during pulling, and the clamping pressure is 10% higher than the pulling force.

34. The method of claim 25 wherein there is more than one die, and the dies are placed at intervals of 0.5 to 500 cm.

35. The method of claim 25 wherein there is a series of dies placed at intervals with hole sizes decreasing in diameter by 0.1 to 10 mm, and the rod stock is pulled through these dies to form the profile.

\* \* \* \* \*